United States Patent [19]

Topal et al.

[11] Patent Number: 5,248,600
[45] Date of Patent: Sep. 28, 1993

[54] METHOD OF CLEAVING DNA

[75] Inventors: Michael D. Topal; Michael J. Conrad, both of Chapel Hill, N.C.

[73] Assignee: The University of North Carolina at Chapel Hill, Chapel Hill, N.C.

[21] Appl. No.: 627,538

[22] Filed: Dec. 14, 1990

[51] Int. Cl.$^5$ .................... C12P 19/34; C12N 9/22
[52] U.S. Cl. .................... 435/91.53; 435/199
[58] Field of Search .................... 435/91, 199

[56] References Cited

PUBLICATIONS

T. Gingeras and J. Brooks, *Proc. Natl. Acad. USA* 80, 402-406 (1983).
D. Krüger et al., *Nucleic Acids Research* 16, No. 9, 3997-4008 (1988).
C. Pein et al., *FEBS Letters* 245, No. 1,2, 141-144 (1989).
Conrad M. et al. (1989) proc. Natl. Acad. Sci., USA 86(24), 9707-9711.

*Primary Examiner*—Charles L. Patterson, Jr.
*Attorney, Agent, or Firm*—Bell, Seltzer, Park & Gibson

[57] ABSTRACT

A method of cleaving substrate DNA with a restriction enzyme, wherein the substrate DNA is resistant to cleavage by the restriction enzyme, is disclosed. The method comprises co-incubating the substrate DNA and the restriction enzyme with an activating DNA sequence. The activating sequence comprises an oligonucleotide comprised of the restriction enzyme recognition site and cleavage permissible flanking sequences joined directly to both the 5' and 3' ends of the recognition site. Exemplary restriction enzymes which may be used in practicing the present invention include Nae I, BspM I, Hpa II, Nar I, and Sac II.

12 Claims, 10 Drawing Sheets

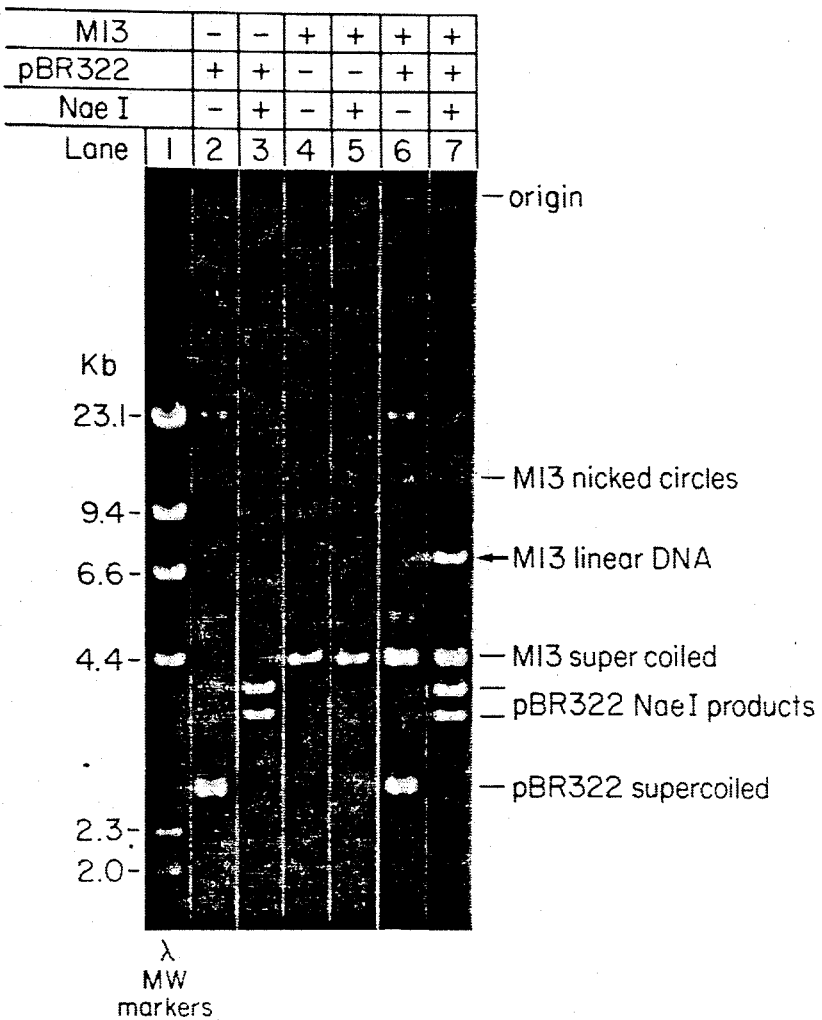
FIG. IA.

|  | – | + |
|---|---|---|
| + DNA | ON | OFF |
| – | OFF | ON |−/+ SPERMIDINE

FIG. 4.

METHOD OF CLEAVING DNA

This work was supported by U.S. Public Health Service grant CA46527. The government may have certain rights to this invention.

FIELD OF THE INVENTION

This invention relates to the cleaving of substrate DNA with restriction enzymes, and particularly relates to methods of enhancing the cleavage of cleavage-resistant substrate DNA.

BACKGROUND OF THE INVENTION

Restriction enzymes, particularly the Type II restriction endonucleases, are used to cut DNA sequences at specific locations. The enzymes carry this out by catalyzing the hydrolysis of phosphodiester linkages (the "scissile linkages") in each polynucleotide strand of a DNA molecule. The Type II restriction endonucleases are valuable for both the analysis of DNA molecules and for recombinant DNA procedures, and there is an ongoing effort to develop new enzymes. See, e.g., N. Brown and E. Walsby, U.S. Pat. No. 4,871,664. Restriction enzymes can be identified by recognition site (that is, the DNA sequence which is recognized and cleaved by a particular enzyme). Knowing the cleavage sites of the various restriction enzymes available enable researchers to cut DNA at the desired location through the selection of the proper enzyme.

A problem with restriction enzymes is that some recognition sites which should be cut by particular restriction enzymes are not. Resistant Eco RII restriction sites exist (S. Hattman et al., J. Virol. 32, 845 (1979)) in $\phi$X174 DNA that can be cleaved in the presence of an uncharacterized, heterologous "stimulator DNA". Resistant Eco RII sites have also been reported (D. H. Kreuger, et al., Nucleic Acids Res. 16, 3997 (1988); C. Pein et al, FEBS Letters 245, 141 (1989)) in phage T3 and T7 DNAs. These were cleaved in the presence of a high density of cleavable Eco RII DNA sites so the authors suggest that at least two bound recognition sites are needed for cleavage (Kruger et al., supra). No kinetics were measured, however, and the basis for the activation was not pursued. The authors reported that spermidine does not affect the Eco RII cleavage of the resistant sites. However, since the concentration range over which spermidine activates cleavage of slow and resistant sites is narrow, the effect could easily have been missed; the concentrations of spermidine used in the study (Kruger et al., supra) were not reported.

Also PaeR7, a type II restriction enzyme from Pseudomonas aeruginosa, shows a resistant site in Ad2 DNA in the presence of other susceptible Ad2 DNA sites (T. Gingeras and J. Brooks, Proc. Natl. Acad. Sci. U.S.A. 80, 402 (1983)); resistance was overcome by replacement of upstream sequences with sequence from a different source. When the gene for PaeR7 was expressed in E. coli, the bacteria were unable to restrict the growth of incoming phage even though cell extracts displayed the expected restriction activity on the phage DNA (Gingeras et al., supra); the authors speculate that this may indicate the presence of a control element.

The present invention is based on our ongoing research in the regulation of restriction enzyme activity.

SUMMARY OF THE INVENTION

A method of cleaving substrate DNA with a restriction enzyme, wherein the substrate DNA is resistant to cleavage by the restriction enzyme, is disclosed. The method comprises co-incubating the substrate DNA and the restriction enzyme with an activating DNA sequence. The activating sequence comprises an oligonucleotide comprised of the restriction enzyme recognition site and cleavage permissible flanking sequences joined directly to both the 5' and 3' ends of the recognition site. Exemplary restriction enzymes which may be used in practicing the present invention include Nae I, BspM I, Hpa II, Nar I, and Sac II.

Also disclosed is a method of cleaving substrate DNA with a restriction enzyme, wherein the substrate DNA is resistant to cleavage by the restriction enzyme, by co-incubating the substrate DNA and the restriction enzyme with a cationic activator, with the cationic activator included in an amount effective to facilitate cleavage of the substrate DNA by said restriction enzyme.

A third aspect of the present invention is a method of cleaving substrate DNA with a restriction enzyme, wherein the substrate DNA is resistant to cleavage by the restriction enzyme, by co-incubating the substrate DNA and the restriction enzyme with an activating DNA sequence as described above, wherein at least one scissile linkage of the activating sequence recognition site is modified to render it incapable of hydrolysis by the corresponding restriction enzyme.

The foregoing and other aspects of the present invention are explained in the drawings and text which follow.

BRIEF DESCRIPTION OF THE DRAWINGS

Figure 4:
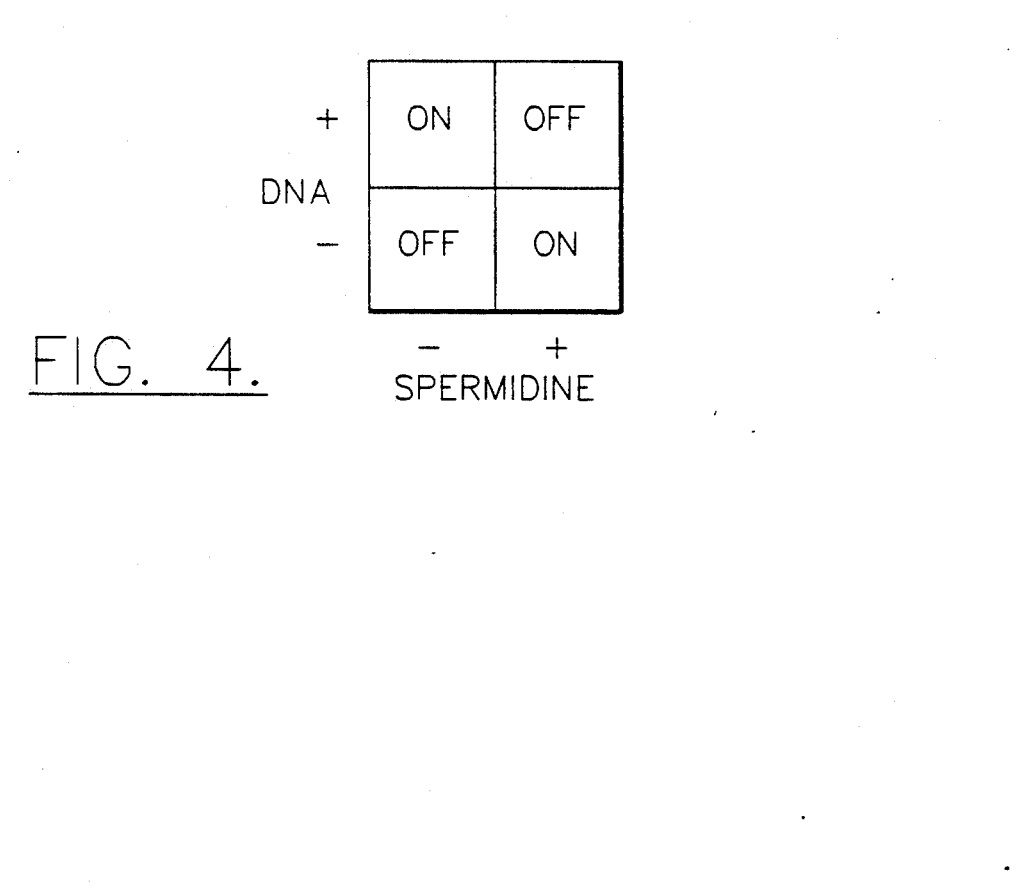

FIG. 4. Possible switch mechanism for control of Nae I cleavage of resistant sites. Interplay of regulator DNA and spermidine control the switch: +spermidine means physiological concentration; +DNA means the presence of genomic sequences available for enzyme binding.

DETAILED DESCRIPTION OF THE PREFERRED EMBODIMENTS

Figure 1B:
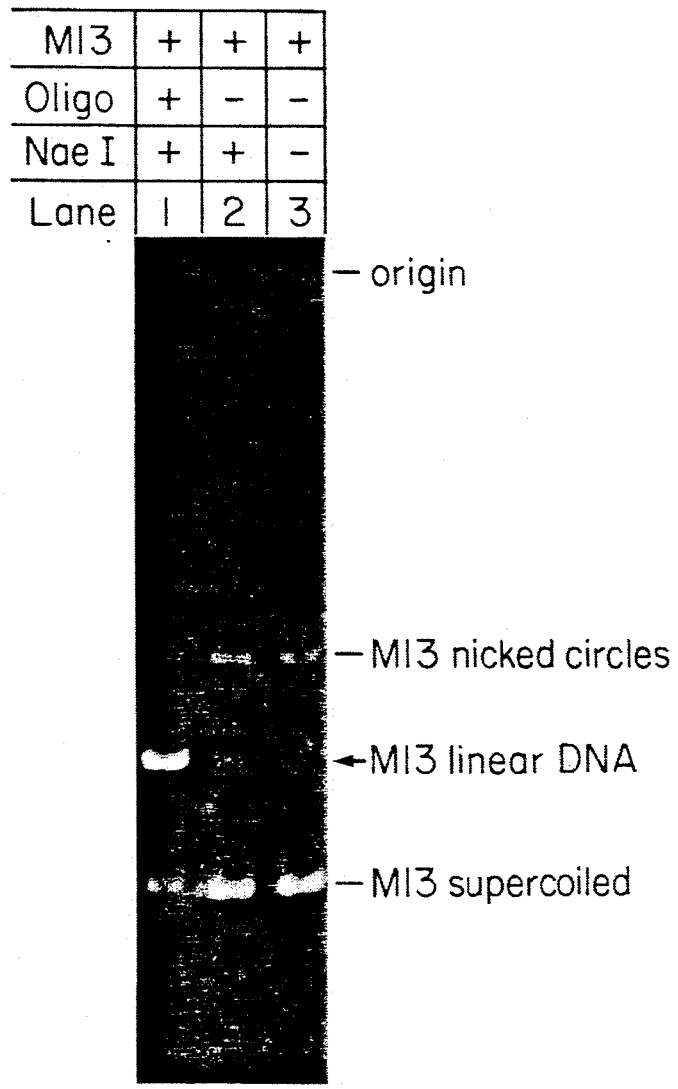
FIG. 1. Activation of Nae I cleavage of a resistant site in M13mp18 RFI DNA by DNA. a) Lane 1 contains a Hind III digest of lambda DNA (New England Biolabs) for molecular weight determination. Lanes 2 & 3 show effect of Nae I on pBR322 (isolated by established procedures), lanes 4–7 show effect of Nae I on M13mp18 RFI DNA with and without the presence of pBR322 DNA. Note the production of linear M13mp18 DNA at the height of the arrow only in lane 7. b) M13mp18 RFI DNA (2.6 nM), lane 3, was cleaved by Nae I in the presence of oligonucleotide duplex #1 (5.2 nM) (Table 2), lane 1, but not in its absence, lane 2.

Nucleotide sequences disclosed herein are displayed in the 5' to 3' direction, from left to right. Where duplex DNA is disclosed the upper strand is displayed in the 5' to 3' direction.

The present invention may be used to cleave any substrate DNA, whether for gene cloning or gene sequencing purposes. The reaction is typically carried out in an aqueous buffer solution containing substrate DNA and a restriction enzyme. It will be appreciated that the substrate DNA is double stranded, and (when a predetermined site is to be cleaved) contains at least one recognition site for said restriction enzyme. Cleavage-resistant DNA may contain either resistant or slow cleavage sites, as will be made apparent below.

Aqueous buffers for use in practicing the present invention generally contain $Mg^{+2}$ in an amount sufficient to enable a Type II restriction enzyme to cleave substrate DNA (i.e., between about 1 and about 20 mM, more preferably about 10 mM), have a pH of between about 6 and about 8 (preferably about 7.4 to about 8), and have a $Na^+$ concentration of from about 0 to about 100 mM. For example, a suitable aqueous buffer solution may contain 20 mM NaCl, 10 mM $MgCl_2$, and 10 mM Tris buffer, adjusted to a pH of about 8.0 with HCl. The buffer may optionally contain about 0.1 mg/ml of bovine serum albumin as a stabilizer and 5 milliMolar 2-mercaptoethanol as a reducing agent. Novel buffers may be created by adding the activating sequences and/or cationic activators described herein.

Activating sequences employed in carrying out the present invention are DNA duplexes which are preferably not more than about 50 nucleotides in length, and more preferably not more than about 25 nucleotides in length. The activating sequences may have unphosphorylated ends and/or have blocking groups covalently joined to one or more ends thereof to ensure that the oligonucleotide will not ligate to other sequences in the reaction mixture.

The recognition sites in the activating sequences of the present invention are flanked on both the 5' and 3' ends by cleavage-permissible flanking sequences which are at least three, and preferably four, nucleotides long.

Cationic activators of the present invention include spermidine, spermine, and cobalt hexamine. These cations have their best activating effect through a relatively narrow concentration range, with the optimum concentration of cationic activator depending on the ionic strength of the buffer solution. The relation between optimum cationic activator concentration and ionic strength is essentially linear. Typical buffer solutions will have an ionic strength of from about 15 to about 90 milliMolar. For such solutions, spermidine may be included in an amount of from about 1 to about 8, or more preferably from about 3 to about 5, milliMolar.

Oligonucleotide recognition sites employed in the present invention, unless specified to the contrary, contain a scissile internucleotide phosphodiester linkage of the formula:

(I)

The scissile phosphodiester linkage is the linkage in each chain of the double-stranded DNA sequence which is hydrolyzed by the restriction enzyme to thereby cleave the recognition site. As noted above, one or both scissile linkages in an activator sequence may be modified to render the activator sequence resistant to hydrolysis by the restriction enzyme. This serves to prevent the activating sequences from being themselves cleaved and rendered non-activating during the reaction procedure. Exemplary of such modified scissile linkages are those having the formula:

(II)

wherein X and X' are each independently O or S; and Y is $O^-$, $CH_3$, OR, or $NR_2$ wherein R is lower alkyl; subject to the proviso that X and X' are not simultaneously O when Y is $O^-$. The methylphosphonate (Y is $CH_3$) of Formula (II) above may be made in accordance with known techniques. See P. Miller et al., 18 *Biochemistry* 5134 (1979). Other modifications may also be made in accordance with known techniques, including the phosphotriester (Y is OR) See P. Miller et al., 93 *J. Am. Chem. Soc.* 6657 (1971); the phosphorothioate (X or X' is S), See P. Burgers and F. Eckstein, 18 *Biochemistry* 592 (1979), the phosphorodithioate (X and X' are S), See W. Brill et al. 111 *J. Am. Chem. Soc.* 2321 (1989), and the phosphoramidate (Y is $NR_2$), See K. Ogilvie and J. Nemer, 21 *Tetrahedron Lett.* 4145 (1988). The term "lower alkyl" as used herein means C1-C4 alkyl such as methyl or tert-butyl, preferably C1-C2 alkyl.

Restriction enzymes are now isolated by conventional enzyme purification methods involving salt fractionation and multiple column chromatographic methods. The discovery of recognition sites resistant to cleavage provides a better method of isolation by affinity chromatography. The DNA containing the resistant site is affixed to suitable chromatography matrix as a solid support and the cell extract containing the cognate enzyme chromatographed over the new DNA-containing matrix; retained enzyme is eluted from the matrix by means of washing the matrix with appropriate high salt buffers. The affinity matrix may be prepared by several standard methods, which include either baking the DNA onto powdered cellulose to produce a DNA-cellulose matrix (B. Alberts et al., Cold Spring Harbor Symp. Quant. Biol. 33, 289 (1968) or covalently cross-linking the DNA to agarose beads using cyanogen bromide as the coupling agent (D. J. Arndt-Jovin et al., *Eur. J. Biochem.* 54, 411 (1975). A new alternative method which takes advantage of the very tight complex formed between biotin and avidin (Kd approx. $10^{-15}$ M) is described in Example 4 below.

The Examples which follow are illustrative of the present invention, and are not to be construed as limiting thereof.

EXAMPLE 1

DNA and Spermidine Provide a Unique Switch Mechanism to Regulate the Activity of Restriction Enzyme Nae I The Type II restriction-modification systems, like the repressors, are important model systems for sequence-specific DNA-protein interactions that are basic to many biological processes. See P. Modrich, Q. Rev. Biophys. 12, 315 (1979); M. Ptashne, A Genetic Switch (1986)(Cell & Blackwell, Palo Alto, Calif.). In the course of studying these interactions, we made the quite unexpected discovery that cleavage by the Type II restriction enzyme Nae I can be controlled by specific DNA sequences; the ability to cleave and the action of external DNA sequences were in turn dramatically affected by spermidine.

Nae I is isolated from *Nocardia aerocolonigenes*, a member of a common family, Nocardiaceae, of soil actinomycetes. It cleaves within the sequence GCC/GGC, with "/" indicating the position of the scissile linkage, and like other Type II enzymes, requires only $Mg^{2+}$ for activity and exhibits only a single function, cleavage. See, e.g., R. Roberts, Nucleic Acids Res. 15, Suppl., r189 (1987). Using commercially available Nae I, we found DNA sequences containing Nae I recognition sites that were cleaved rapidly and Nae I sites that were almost totally resistant to cleavage. Studies of Nae I interaction with these sites show that Nae I was activated to rapidly cleave resistant sites and that the activator was a cleavable Nae I site. The activated cleavage reaction followed Michaelis-Menten kinetics, which indicated that activation was non-competitive and worked by increasing catalysis rather than by increasing the affinity of enzyme for its substrate. Deletion mutagenesis in vitro showed that sequences flanking the Nae I recognition site were responsible for the enzyme-regulatory properties of the cleavable sites. Spermidine could reverse the effect; in the presence of 1 mM spermidine, resistant sites were cleaved rapidly but cleavable DNA inhibited their cleavage providing a novel regulatory switch mechanism.

A. MATERIALS AND METHODS

Restriction enzyme cleavage reactions were performed in 10 μl containing 0.15 μg (2.6 nM) M13mp18 RFI DNA (New England Biolabs) or pBR322 DNA, 2 units of Nae I (reported to be >95% pure; New England Biolabs) where indicated, 2 mM NaCl, 1 mM Tris-HCl (pH 8.0), 1 mM $MgCl_2$, 0.5 mM 2-mercaptoethanol, and 0.1 μg bovine serum albumin. Equal concentrations (molecule basis) of oligonucleotide duplex were added in addition to M13mp18 DNA where indicated. pBR322 DNA (0.15 μg) was added where indicated (a 40% molar excess to M13mp18 DNA). Reactions were incubated at 37° C. Qualitative reactions shown in gel pictures were incubated for 1 hr; quantitative reactions to determine kinetics of cleavage were incubated for 20 min to be sure we were within the linear range of the cleavage reaction, which was determined to be at least 40 min. The reactions were then stopped by placing on ice, electrophoresed on a 1% agarose gel, and the gel stained with ethidium bromide and photographed under ultraviolet light.

DNA oligonucleotides were synthesized by machine (Applied Biosystems Model 380A). The two longest oligonucleotides were purified by gel electrophoresis and eluted from the appropriate gel slice and precipitated with alcohol. The other oligonucleotides were used directly after precipitation with alcohol.

Nae I cleavage reactions were monitored by quantitative gel assays. Products of Nae I cleavage were separated by agarose gel electrophoresis; the DNA bands were visualized by ethidium bromide staining, and the cleavage measured by densitometric analysis of photographic negatives. This method is quantitative (R. Depew and J. Wang, Proc. Natl. Acad. Sci. U.S.A. 72, 4275 (1975)) and has the advantage of detecting reaction intermediates such as nicked circles in the case of supercoiled substrates.

B. RESULTS

Analysis of Susceptibility to Cleavage by Nae I.

A small survey of DNAs uncovered single Nae I sites that were resistant to cleavage (Table 1 & FIG. 1); resistance was defined as the inability of 2 units of Nae I to significantly cleave a site contained in 0.15 μg of DNA in one hour at 37° C. This resistance was independent of supercoiling since supercoiled and linear bacteriophage M13mp18 (C. Yanisch-Peron et al., Gene 33, 103 (1985)) double-strand DNA were resistant to cleavage by Nae I.

Cleavable sites were found in both multisite DNAs and DNAs containing unique sites. The rates of cleavage appeared to vary up to five-fold among the cleavable sites studied. However, the resistant sites were uniquely separable as a class from the cleavable sites.

It was possible that a contaminant in the preparations of some of the DNAs was responsible for their resistance to cleavage by Nae I. Therefore, resistant M13mp18 and cleavable pBR322 DNAs were added in the same reaction to see if cleavage of pBR322 was inhibited (FIG. 1). Surprisingly, resistance of M13mp18 DNA to cleavage by Nae I was overcome by the presence of pBR322 DNA. DNAs with only resistant sites did not overcome the resistant Nae I site in M13mp18

DNA (Table 1); this is consistent with the inability of M13mp18 DNA to enable its own cleavage (FIG. 1). Addition of other cleavable sites, but not resistant sites, were found to overcome resistance to cleavage by Nae I (Table 1).

TABLE 1

Cleavage of Nae I Recognition Sites in Various DNAs

| DNA[1] | Conformation[2] | No. of Sites | Cleaved[3] | Activating[4] | Activated[5] |
|---|---|---|---|---|---|
| pBR322 | sc. nk. or lin | 4 | Yes | Yes | No |
| | Nae I precut | 0 | | No | |
| pBR322 fragments | | | | | |
| Site 1283 | 2319 bp | 1 | Yes | Yes | No |
| 401 plus 769 | 1810 bp | 2 | Yes | Yes | No |
| 401 (pSP64) | sc | 1 | No | No | Yes |
| M13mp18 | | | | | |
| Site 5613 | sc, nk, or lin | 1 | No | No | Yes |
| 5613 (pUC-f1) | sc | 1 | No | No | Yes |
| DHFR-pUC18 | sc | 1 | No | No | Yes |
| pSV2 | | | | | |
| Sites 1326 and 1609 | lin | 2 | Yes | Yes | No |
| 1326 (pMC1neo) | sc | 1 | No | No | Yes |
| R208 | sc or lin | 5 | Yes | Yes | No |
| | ss | 0 | | No | |
| Oligomer duplex 1 | ds | 1 | Yes | Yes | |
| | ss | 0 | No | No | |

[1]Coordinates are for the first 5' base of Nae I recoginition sequence. Some phage and plasmid Nae I sites, defined as recognition sequence plus at least 25 bases each of 5'-and 3'-flanking sequence, exist on other plasmids: pBR322 Nae I site 104 is the only Nae I site in pSP64 (Boehringer Mannheim) (see text); pUC-f1 (Pharmacia) contains M13mp18 sequence [Nae I site plus 127 base pairs (bp) of 5'-and 388 bp of 3'-flanking sequence]; pSV2 contains only two Nae I sites (R. Schleif, Science 240, 127-128 (1988)), one of which (with 624 bp of 5'-and 163 bp of 3'-flanking sequence) resides in pMClneo (D. Chattoraj et al., Cell 52, 551-557 (1988)) (Strategene). DHFR-pUC18 (gift of Jane Azizkhan, Lineberger Cancer Research Center, University of North Carolina) contains 216 bp of the hamster dihydrofolate reductase gene (nucleotides −238 to −23 on the map as per J. Azizhan, Biochemistry 25, 6228-6236 (1986)), including a single Nae I site and 51 bp of 5'- and 159 bp of 3-'flanking sequence. R208 contains M13mp18 and pBR322 in the same molecule (J. Boeke et al., Proc. Natl. Acad. Sci USA 76,2699-2702 (1979)).
[2]sc, Supercoiled; nk, nicked; lin, linear; ss, single-stranded; ds, double-stranded. Linear molecules were precut at unique, non-Nae I restriction sites. Precutting with Nae I was used to destroy all Nae I sites in pBR322.
[3]Cleaved by Nae I in the absence of additional DNA or spermidine.
[4]Activating Nae I cleavage of M13mp18 double-stranded supercoiled DNA.
[5]Activated by the cleavable Nae I site contained in oligonucleotide duplex 1 (see Table 2).

This activation of the enzyme to cleave resistant sites was independent of supercoiling since supercoiled, relaxed, and linear pBR322 equally activated Nae I to cleave M13mp18 DNA. Activation was dependent on the presence of a cleavable site; neither pBR322 precut with Nae I nor DNAs without Nae I sites activated Nae I to cleave double-stranded M13mp18 DNA (Table 1). Nae I activity at cleavable sites was not enhanced by addition of other DNAs. Of course, the addition of high concentrations of other sites reduced cleavage due to competition for enzyme.

The requirement for cleavable sites suggested that Nae I required two bound recognition sites for activity. Any two sites were not sufficient; one of those sites had to be cleavable.

Are All Nae I sites in pBR322 DNA Cleavable?

The four Nae I sites in pBR322 (nucleotides 401, 769, 929, and 1283 on the map as per J. Sutcliff, *Cold Spring Harbor Symp. Quant. Biol.* 43, 77 (1979) & K. Peden *Gene* 22, 277 (1983); the coordinate of the first 5' base of the recognition sequences is given) are all cleavable, but at different rates. One, nucleotide 401, is cleaved rapidly, one (nucleotide 1283) is cleaved about 5-fold slower, and the other two fall in-between (not shown). We restricted pBR322 DNA using Bgl II and isolated two of the fragments. One contained the nucleotide 1283 Nae I site by itself, the other contained the Nae I site at nucleotide 401 together with the site at 769. We took advantage of the fact that a fragment of pBR322 DNA containing the Nae I site at nucleotide 401 and 35 base pairs of 5'- and 250 base pairs of 3'-flanking sequence reside as the only Nae I site in the plasmid pSP64 as a consequence of its ancestry. See D. Melton et al., Nucleic Acids Res. 12, 7035 (1984). The nucleotide 401 Nae I site by itself on pSP64 was resistant to cleavage; the nucleotide 401 site when together with the nucleotide 769 site on the same DNA fragment was cleaved; the nucleotide 1283 site by itself was cleavable, but still reflected the slower rate it demonstrated when part of pBR322 (Table 1). These results show that: a) although all Nae I sites in pBR322 are apparently cleavable, in actuality pBR322 contains a mixture of cleavable sites and resistant sites that interact; and b) the phenomenon of resistance to enzyme cleavage appears unrelated to the 5-fold difference in cleavage at the nucleotide 1283 site, mentioned above.

Kinetics of Activated Cleavage by Nae I.

The ability of cleavable, but not resistant Nae I sites to activate the enzyme indicates a possibly important effect of DNA sequence outside the recognition site on enzyme binding or catalysis. Therefore, a series of oligonucleotides was used that contain an Nae I site and varying lengths of flanking sequences (Table 2). Oligonucleotide duplex #1 (Table 2) contained an Nae I cleavable site and was about as effective as an equal concentration of Nae I sites in pBR322 at activating Nae I cleavage of M13mp18 DNA (FIG. 1).

TABLE 2

Deletion Analysis of Oligonucleotide Activation of Nae I

| No. | Oligonucleotide Duplex[1] | Activation[2] |
|---|---|---|
| 1) | CTAGCTGGTGGTGGGCGCCGGCGGTGTGGGCAGCTGGTGAGCT<br>GACCACCACCCG<u>CGGCCG</u>CCACACCCGTCGACCAC | + + + + |
| 2) | TGGTGGGCGCCGGCGGTGTGGGCA<br>ACCACCCG<u>CGGCCGC</u>CACACCCGT | + + + + |
| 3) | GGGCGCCGGCGGTG<br>CCCG<u>CGGCCGC</u>CAC | + + |
| 4) | GCGCCGGCGG<br>CG<u>CGGCCGC</u>C | – |
| 5) | CTGGTGGTGGGCGCCGGC<br>GACCACCACCCG<u>CGGCCG</u> | – |
| 6) | GCCGGCGGTGTGGGCAGCTGGT G<br><u>CGGCCGC</u>CACACCCGTCGACCAC | – |
| 7) | GCCGGC<br>CGGCCG | – |

[1]Nae I recognition site is underlined. The top strand shown for nos. 1-7 are SEQ ID NO:2, SEQ ID NO:3, SEQ ID NO:4, SEQ ID NO:5, SEQ ID NO:6 SEQ ID NO:7 AND SEQ ID NO:1, respectively
[2]Activation of Nae I cleavage of M13mp18 RF1 DNA as compared to cleavage caused by an equal concentration of pBR322 Nae I sites: + + + +, full activation; + +, about 50% activation; –, no activation.

Figure 2A:
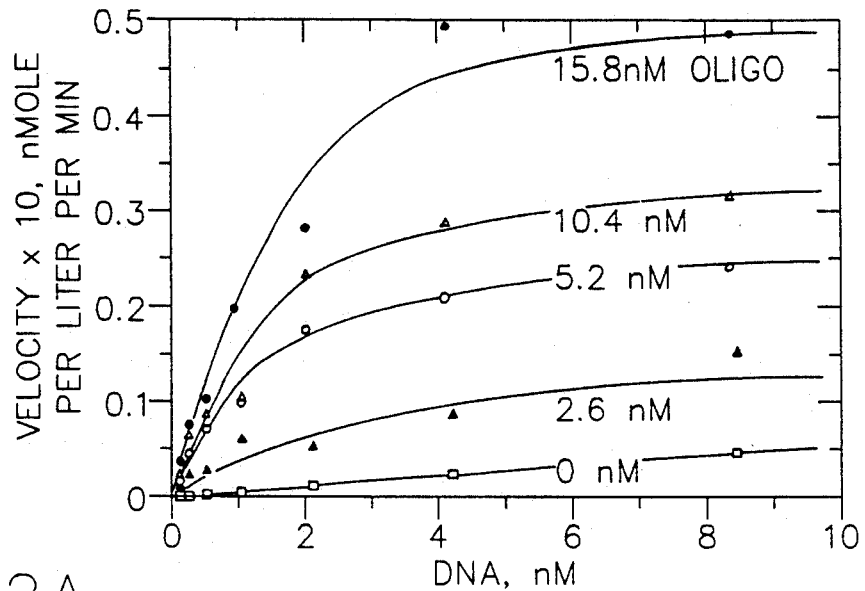
FIG. 2. Kinetics of Nae I cleavage of M13mp18 RFI DNA. a) Reactions were performed as described in FIG. 1 legend except reactions were stopped after 20 min. Oligonucleotide duplex #1 was added to the indicated concentration. Agarose (1%) gels were photographed and negatives scanned using a densitometer (Bio-rad 1650). Linear DNA product is proportional to peak area (D. Melton et al., Nucleic Acids Res. 12, 7035 (1984)). b) Eadie-Scatchard plot of kinetic results (I. Segel, Enzyme Kinetics, 214–218 (Wiley, NY 1975)); $K_m = -1/\text{slope}$, $V_{max}$ is x-intercept.
Figure 2B:
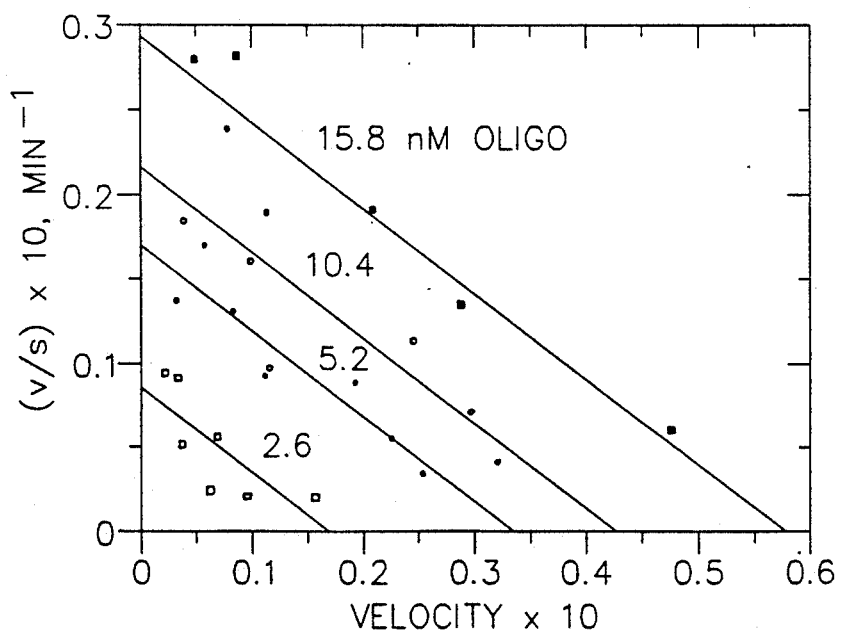

Cleavage of M13mp18 DNA, activated by this oligonucleotide duplex, was linear for at least 40 min. under our conditions (not shown). Increasing concentrations of activating oligonucleotide and increasing M13mp18 DNA substrate concentrations gave higher velocities of Nae I cleavage (FIG. 2a). Activated Nae I obeyed Michaelis-Menten kinetics; an Eadie-Scatchard plot of the kinetic results (FIG. 2b) showed a $K_M$ of 2 nM for Nae I recognition site that was independent of activator concentration. $V_{max}$, however, varied with activator concentration (FIG. 2b). The magnitude of $K_M$ is similar to that for Eco RI (P. Modrich and D. Zabel, J. Biol. Chem. 251, 5866 (1976), which also recognizes 6 base pairs, and is similar to the binding constant for lambda repressor binding to operator sequence (M. Ptashne, supra).

Determination of $K_A$ for oligonucleotide #1 from a replot of the kinetic results of FIG. 2a in terms of varying activator concentration at constant M13mp18 concentration gave a $K_A$ of about 6 nM; $K_A$ was also determined from the slope ($= -K_A$) of a linear plot of the Y-intercept of FIG. 2b against Y-intercept/[activator] to be about 10 nM (not shown).

The characteristics of the kinetic results fit the classical model for noncompetitive activation in which the effector has no affect on substrate binding, and vice versa. According to this model, the effector and the substrate bind reversibly, randomly, and independently at different sites (I. Segel, Enzyme Kinetics, pp. 125, 400 (Wiley, NY 1975)). M13mp18 DNA was cleaved so poorly by unactivated Nae I that the reaction can be considered to be pure rather than partial noncompetitive activation (FIG. 2a), in agreement with the classical model; this model assumes that binding of activator distorts the enzyme to properly position the catalytic center so that the enzyme/substrate/activator complex is productive (I. Segel, supra at 125-129).

The noncompetitive mechanism is not obligate for all Nae I sites since the kinetics for cleavage of the oligonucleotide activator was found to be first order (unpublished results) indicating binding at only a single site was required for cleavage of cleavable sites. The $K_M$ for cleavage of the oligonucleotide activator duplex was 246 nM; this value supports the existence of two binding sites with different affinity for the activating oligonucleotide duplex; the activating site with $K_A$ for the oligonucleotide duplex of 6-10 nM and the substrate binding site with $K_M$ of 246 nM for this same molecule. The high $K_M$ for cleavage of the activator, 246 nM, compared to that for cleavage of M13mp18, 2 nM, explains why the Eadie-Scatchard plots were linear in the presence of two potentially competing substrates.

Flanking Sequences Affect Activation.

Since only cleavable sites activated Nae I, there must be DNA sequences external to the recognition site that, together with Nae I recognition site, define susceptibility to cleavage and enable activation. Our results with oligonucleotide duplex #1 specifically indicated the presence of such sequences within this relatively short duplex. To better define those sequences, we deleted regions from one or both recognition-site flanking sequences (Table 2). The results indicate that sequences responsible for activation, in addition to the Nae I cognate recognition site, are located mostly within about 8 to 10 bases of flanking sequence on both sides of the Nae I site.

Spermidine Changes Resistant Sites into Cleavable Sites and Activation into Inhibition Changes in DNA conformation can be potentiated by particular cations such as spermidine See W. Zacharias et al., J. Biol. Chem 257, 2775 (1982); J. van de Sande et al., EMBO J. 1, 777 (1982); K. Sullivan and D. Lilley J. Biol. Chem. 193, 397 (1987); C. Laundon and J. Griffith, Biochemistry 26, 3759 (1987). These polymorphic variations have been detected because of the easily measured changes in physical properties associated with the alterations. However, it is likely that a range of structural variation is possible. Therefore, we tested spermidine at 1 mM for its effect on Nae I activation.

Figure 3A:
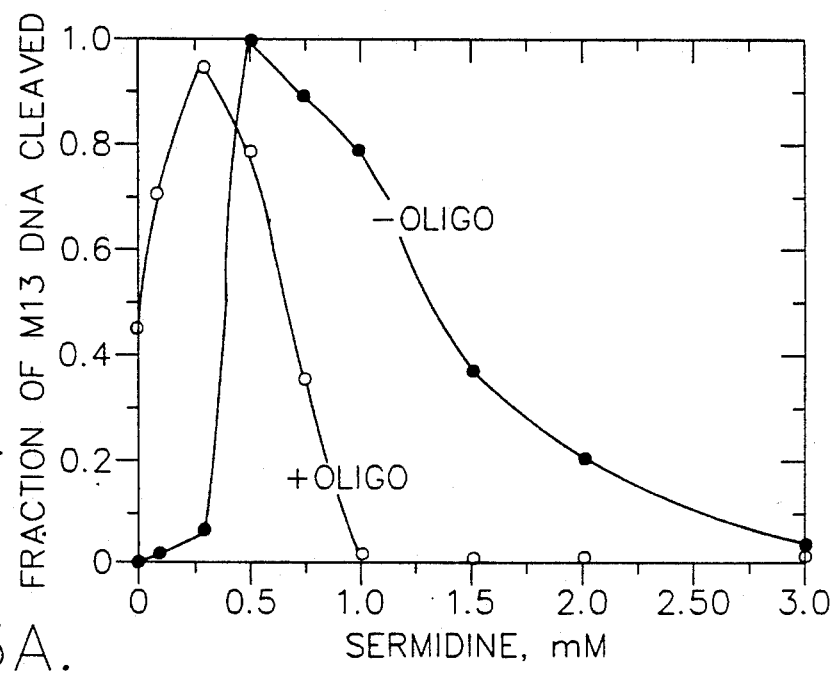
FIG. 3. Effect of spermidine on Nae I cleavage of M13mp18 RFI DNA. Reaction conditions were the same as that described in Materials and Methods except that reactions were stopped after 20 min. and [M13mp18 DNA] was 3.4 nM. [Oligonucleotide] was 15.8 nM. Insert shows the gel results for some of the spermidine concentrations. Note the opposing effects of spermidine on linear M13mp18 production depending on the presence or absence of oligonucleotide.
Figure 3B:
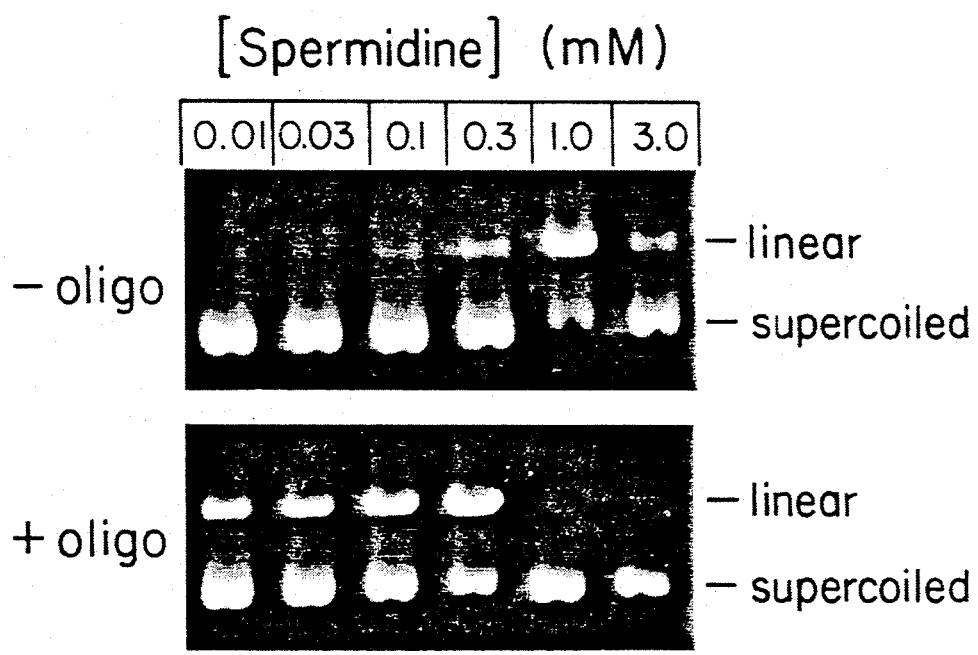

Spermidine at 1 mM greatly activated the cleavage of resistant Nae I sites such as in M13mp18 DNA, but had little affect on cleavable sites. Perhaps most surprising, addition of oligonucleotide duplex #1 completely inhibited Nae I cleavage of M13mp18 in the presence of 1 mM spermidine. Analysis of the affect of a wider range of spermidine concentration on Nae I cleavage (FIG. 3) showed that Nae I cleavage of resistant sites is switched on by either: a) cleavable Nae I sites in the presence of low to no spermidine or b) about 1 mM spermidine by itself. And cleavage is switched off by either: a) the combination of low to no spermidine and no cleavable sites or b) the combination of about 1 mM spermidine and cleavable sites.

As expected, the effect of spermidine on Nae I cleavage was dependent on the overall cation concentration; other cations compete with spermidine for binding to DNA. For example, at 1 mM $Mg^{2+}$ and 50 mM $Na^+$, it took spermidine at 6 mM to mimic the affect spermidine had at only 1 mM (not shown) on Nae I under low salt conditions (conditions given in Materials and Methods).

EXAMPLE 2

The Ability of DNA and Spermidine to Affect the Activity of Restriction Endonucleases from Several Bacterial Species Example 1 above describes the ability to control in vitro the activity of the type II restriction endonuclease Nae I isolated from *Nocardia aerocolonigenes*. The ability to control the activity of the type II restriction enzyme Nae I in vitro and reports that Eco RII, another type II restriction enzyme, can be activated by exogenous DNAs (Hattman et al., supra and Kruger et. al., supra) raised the question of whether this possible regulatory mechanism is more widely found among bacterial species. To look for this activation mechanism in other bacterial species, we surveyed 49 enzymes (including Nae I) for the presence of resistant sites whose cleavage could be activated by cleavable DNA and spermidine.

The kinetics of cleavage for these enzymes were measured; resistant sites were identified for BspM I, Nae I, and Nar I. In addition, sites that were cleavable, but with much slower kinetics, were identified for Hpa II, Nae I and Sac II. Cleavage of resistant and slowly cleaved sites was significantly enhanced by the addition of cleavable DNA or spermidine. Thus, although these restriction enzymes were isolated from different microorganisms, we demonstrate that they share a similar activating mechanism to the one previously described for Nae I endonuclease.

A. Materials and Methods

DNA substrates. pBR322 and $\phi$X174 DNAs were purchased from Promega (Madison, Wis.); M13mp18 and pSP64 DNA were purchased from Boehringer Mannheim (Indianapolis, Ind.), SV40 DNA was purchased from Bethesda Research Laboratories, (Gaithersburg, Md.) and pUC-f1 DNA was purchased from Pharmacia (Piscataway, N.J.). Plasmid pMB3 (DHFR-pUC18) was a gift from Dr. Jane Azizkhan, Lineberger Comprehensive Cancer Center, University of North Carolina.

Restriction Endonucleases. The following enzymes were purchased from New England Biolabs (Beverly, Mass.): Aat II, Afl II, Ase I, Ban I, Bgl I, BspM I, BssH I, BstB I, Dra III, Eag I, Fsp I, Msc I, Nae I, Nci I, Nru I, Sca I, Sma I, Ssp I. The following enzymes were purchased from Bethesda Research Laboratories (Gaithersburg, Md.): Ava I, Ava II, Bcl I, Bgl II, Cla I, Hae II, Hpa II, Hind III, Msp I, Nae I, Nar I, Nde I, Pst I, Pvu I, Pvu II, Sal I, Xho I, Xma III. The enzymes Acc I, Apa I, BamH I, EcoR V, Kpn I, Nhe I, Sac II, Sfi I, Sph I, Stu I, Taq I and Xba I were purchased from Promega (Madison, Wis.). EcoR I and Crf10 I were purchased from U.S. Biochemicals (Cleveland, Ohio).

Reaction Conditions. Reactions were typically performed in the presence of 100–200 ng of substrate DNA in a 10 ml volume. The manufacturer's definition of a unit of restriction enzyme activity is that amount of enzyme needed to cleave 1 mg of DNA to completion, after a 60 min incubation at 37° C., in a 50 ml volume. This standard DNA is usually from bacteriophage Lambda or Adenovirus-2 (Ad2) and the number of restriction sites varies with the enzyme. To correct for the different number of recognition sequences in these DNAs for each of the different enzymes, we corrected the manufacturer's unit value for the different enzymes taking into account 1) the mg of DNA used in the reaction, 2) the molecular weight of the substrate and 3) the number of restriction sites in the standard DNA and in the substrate DNA. The activity of restriction enzymes was tested at 1 to 30× equivalent units. Each enzyme was tested in the buffer suggested by the manufacturer. Cleavage reactions were carried out for 60 minutes at 37° C. unless otherwise indicated.

Kinetics. Km measurements were done by varying the concentration of substrate from 1 to up to 60 nM with incubation times between 15 and 40 minutes; the amount of cleavage was kept at less than 10% of the starting material. All kinetic studies were done on supercoiled DNA substrates. The electrophoresis of DNA samples was performed in 1% agarose gels in 1X TAE buffer (40.0 mM Tris Acetate pH 8.0 and 2.0 mM EDTA); the gels were stained with 1 mg/ml of ethidium bromide and photographed using a UV-light transilluminator and polaroid instant film type 665. Negatives from photographs of the gels were scanned on a Bio-Rad Model 1650 densitometer (Hoefer). Scans were analyzed using a Maxima chromatography workstation from Dynamic Solutions Corp. (Ventura, Calif.).

B. RESULTS

Figure 5:
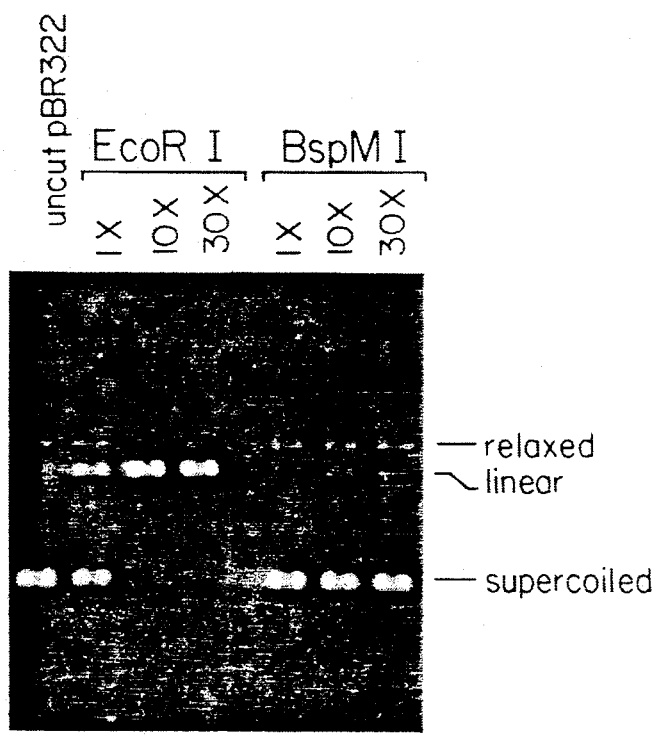
FIG. 5. Cleavage of pBR322 DNA by Eco RI and BspM I endonucleases. The enzymes were added at 1-, 10-, and 30-fold excess as described in Example 2 Materials and Methods. The substrate, pBR322 DNA, was present at 3.5 nM in a 10 ml reaction volume. The reactions were incubated for 1 hour at 37° C.

Presence of Cleavable, Slow and Resistant Sites. Based upon the data presented in Example 1 above, the presence of a cognate recognition site in the DNA does not guarantee cleavage. Therefore, we examined the cleavage of DNA substrates having only one recognition site for each enzyme. Digestion of the DNAs with appropriate restriction enzymes showed the presence of sites that are cleaved at widely different rates. For the purposes of this discussion, we define cleavable, slow and resistant sites for our reaction conditions. A cleavable site is defined as a site where 90% or more of the DNA is cleaved within one hour with a 1- to 5-fold excess of enzyme predicted from its unit activity to be necessary for complete cutting of the single-site substrate. A slow site is defined as a site where between 5% and 90% cleavage is achieved with a 5-fold excess of enzyme; the addition of a 10- or 30-fold excess of enzyme increased cleavage at slow sites. A resistant site is defined as a site at which less than 5% cleavage can be achieved with a 5-fold excess of enzyme; the addition of a 10- to 30-fold excess of enzyme did not increase cleavage at resistant sites. For example, FIG. 5 shows the digestion of pBR322 DNA by two enzymes, EcoR I and BspM I; both of these enzymes have a unique site in this DNA. Plasmid pBR322 DNA was found to have a cleavable Eco RI site, but a resistant BspM I site.

The 49 enzymes surveyed were categorized in terms of their ability to cleave their respective recognition sequence. Table 3 lists the restriction enzymes that had cleavable sites and the substrate DNA used. Table 4 lists the restriction enzymes that had slow or resistant sites. Five of 49 restriction enzymes surveyed showed sites that were slow or resistant. Three of these enzymes, Hpa II, Nae I and Sac II, had substrates that were slow. In addition to Nae I, the restriction enzymes, BspM I and Nar I had substrates that were resistant.

TABLE 3

Restriction Enzymes with Cleavable Sites

| Enzyme | Site[a] | DNA Substrate | Enzyme | Site | DNA Substrate |
|---|---|---|---|---|---|
| Aat II | GACGT/C | pBR322 ϕX174* | Cfr 10 I | U/CCGGY | M13mp18 SV40 |
| Acc I | GT/XMAC | M13mp18 SV40 | Dra III | CACN$_3$/GTG | M13mp18 ϕX174 |
| Afl II | C/TTAAG | SV40 | Eag I | C/GGCCG | pBR322 pMc1neo |
| Apa I | GGGCC/C | SV40 Lambda | EcoR I | G/AATTC | M13mp18 pBR322 |
| Ase I | AT/TAAT | pBR322 | | | SV40 |
| Ava I | C/YCGUG | pBR322 ϕX174 | EcoR V | GAT/ATC | pBR322 SV40 |
| Ava II | G/GZCC | M13mp18 ϕX174 | Fsp I | TGC/GCA | M13mp18 ϕX174 |
| BamH I | G/GATCC | M13mp18 pBR322 SV40 | Hae II | UGCGC/Y | SV40 |
| Ban I | G/GYUCC | SV40 | Hind III | A/AGCTT | M13mp18 pBR322 |
| Bcl I | T/GATCA | SV40 | Kpn I | GGTAC/C | M13mp18 SV40 |
| Bgl I | GCCN$_5$GGC | M13mp18 SV40 | Msc I | TGG/CCA | M13mp18 |
| Bgl II | A/GATCT | M13mp18 | Msp I | C/CGG | SV40 |
| BssH II | G/CGCGC | ϕX174 | Nci I | CC/WGG | ϕX174 |
| BstB I | TT/CGAA | Adeno-2 | Nde I | CA/TATG | M13mp18 pBR322 |
| Cla I | AT/CGAT | pBR322 | | | |
| Nhe I | G/CTAGC | pBR322 Lambda | Sma I | CCC/GGG | M13mp18 |
| Nru I | TCG/CGA | pBR322 | Sph I | GCATG/C | M13mp18 pBR322 |
| Pst I | CTGCA/G | pBR322 ϕX174 SV40 | Ssp I | AAT/ATT | pBR322 ϕX174 |
| | | | Stu I | AGG/CCT | ϕX174 |
| Pvu I | CGAT/CG | M13mp18 pBR322 | Taq I | T/CGA | SV40 |
| Pvu II | CAG/CTG | pBR322 | Xba I | T/CTAGA | M13mp18 Lambda |
| Sal I | G/TCGAC | M13mp18 pBR322 | Xho I | C/TCGAG | ϕX174 Lambda |
| Sca I | AGT/ACT | pBR322 | Xma III | C/GGCCG | pBR322 |
| Sfi I | GGCCN$_5$GGCC | SV40 | | | |

[a] 5' to 3' DNA sequence of the restriction enzyme recognition site from supplier catalogs. /, cleavage position: X, A or C; M, G or T; W, G or C; Z, A or T.
*Considerable nicking.

TABLE 4

Slow and Resistant Restriction Enzyme Sites

| Enzyme | DNA Site | Class[a] | Km (nM) | Vmax (nM/min) | Activation by DNA |
|---|---|---|---|---|---|
| | Resistant Sites | | With Activator | | |
| BspM I ACCTGCN$_4$/ | pUC-f1 | V | 7.0 | d | yes by ϕX174 yes by M13mp18 |
| | pBR322 | | 3.5 | d | yes by ϕX174 yes by M13mp18 |
| Nae I GCC/GGC | M13mp18 | V | 2 | 0.06[c, d] | yes by oligo[f] yes by pBR322 yes by SV40 |
| | pUC-f1 | | 42 | d | yes by oligo |
| | DHFR-pUC18 | | 24.5 | d | yes by oligo |
| | pMC1neo | | 6.6 | d | yes by oligo |
| | pSP64 | | 23.7 | d | yes by oligo |
| | Lambda | | n.d.[b] | | no by pBR322 no by oligo |
| Nar I GG/CGCC | M13mp18 | K | 1.1[c, d] | 0.004 | yes by oligo yes by pBR322 yes by ϕX174 no by Lambda |
| | Lambda | | n.d. | | yes by pBR322 yes by ϕX174 no by M13mp18 |
| | Slow Sites | | Without Activator | | |
| HpA II C/CGG | SV40 | K | 10[c, d, e] | 0.162 | yes by pBR322 yes by oligo |
| Nae I | SV40 | V | 30 | 0.01 | yes by oligo yes by pBR322 |

TABLE 4-continued

| | Slow and Resistant Restriction Enzyme Sites | | | | |
|---|---|---|---|---|---|
| Enzyme | DNA Site | Class[a] | Km (nM) | Vmax (nM/min) | Activation by DNA |
| Sac II CCGC/GG | pMB3 | K | e | e | yes by Ad-2 no by lambda no by $\phi$X174 |
| | $\phi$X174 | | 32 | 0.15 | no by Ad-2 no by lambda no by pMB3 |

[a]Class refers to whether the enzyme is part of a positive allosteric V- or K-system.
[b]Not determined.
[c]Value measured at saturating concentration of activator.
[d]Varied with the amount of activator.
[e]Sigmoidal kinetics without activator.
[f]Double strand DNA containing unique cleavable Nae I, Nar I, and Hpa II restriction sites.

Figure 6A:
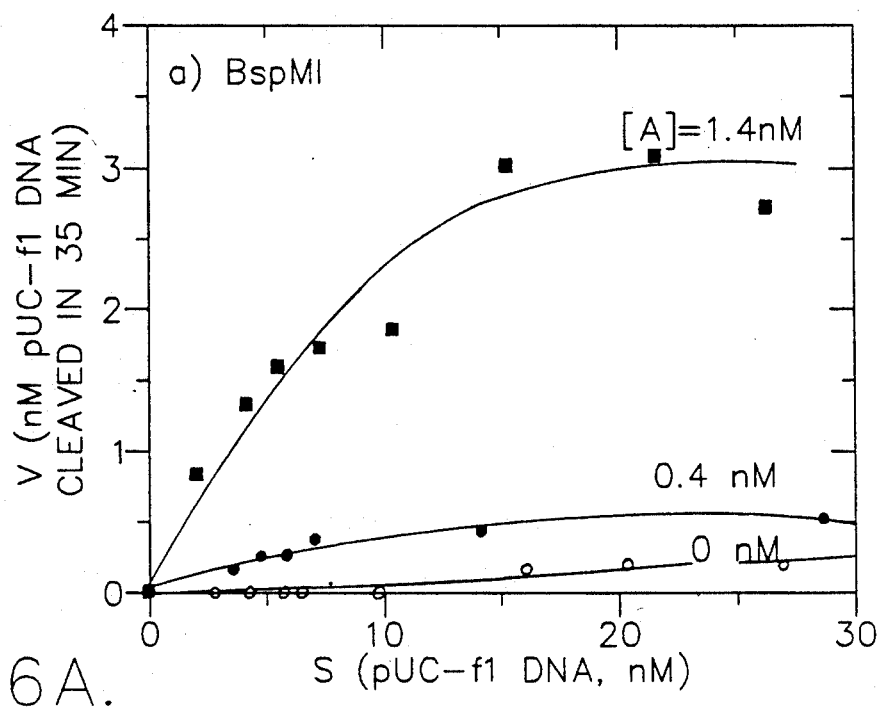
FIG. 6. Allosteric activation of resistant and slow sites. a) V versus S plot for the BspM I resistant site in pUC-f1 DNA. The activator DNA [A] was φX174. 0.8 units of BspM I per reaction were used. b) V versus S plot for the Hpa II slow site in SV40 DNA. The activator DNA [A] was pBR322. The enzyme concentration was 0.12 units per reaction.

Cleavage at Resistant Sites. Table 4 lists the resistant substrates found for BspM I, Nae I and Nar I. All resistant recognition sites showed activation of cleavage by addition of cleavable or slow DNA sites to the reaction. To determine whether the activator DNA affected the Vmax or the Km of the reaction, these parameters were measured in the presence of various concentrations of activator. The Vmax for Nae I cleavage of the resistant M13mp18 DNA site increases with increasing concentration of activator, whereas the Km remains constant (Conrad & Topal, 1989). Similarly, BspM I showed an increase in Vmax for cleavage of the resistant site in pUC-f1 DNA increasing concentrations of activating $\phi$X174 DNA, whereas Km remained constant (FIG. 6a).

For Nar I, however, the Vmax for cleavage of M13mp18 double-stranded DNA remained constant, whereas the Km decreased with increasing concentrations of activator; activator was an oligo duplex DNA containing a Nar I site (Table 4 and Example 1).

In general, resistant cognate recognition sites were unable to activate cleavage of other resistant sites (Table 4). The only exception was the inability of the activating oligonucleotide duplex to stimulate cleavage of the resistant Nae I site in lambda DNA for reasons that we do not understand.

Cleavage at Cleavable Sites. For comparison with enzymes showing slow and resistant sites, the Km and Vmax for cleavage of pBR322 DNA by EcoR I was determined to be 12 nM and 0.3 nM/min, respectively (not shown). The measured Km is similar to the value of 8 nM for cleavage of ColE1 DNA (from which pBR322 DNA was derived) by EcoR I under similar conditions (P. Modrich and D. Zabel, J. Biol. Chem. 251, 5866 (1976)).

Figure 6B:
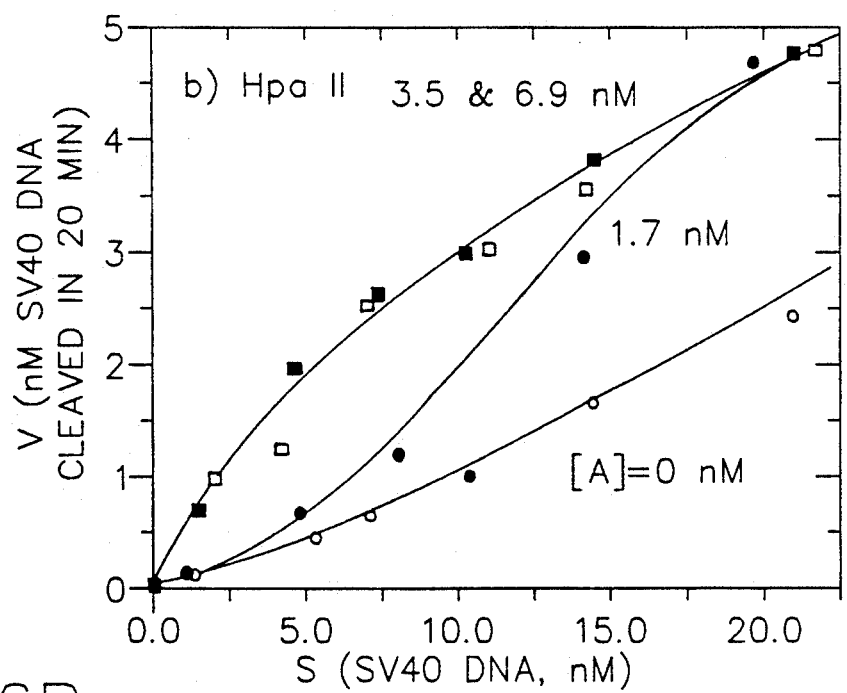

Cleavage at slow sites. For Hpa II (FIG. 6b), the Km for cleavage of its single SV40 DNA recognition site decreased with increasing concentrations of pBR322 activator DNA. The shape of the velocity/saturation curve for Hpa II cleavage of SV40 DNA without activator present was sigmoidal; the shape of the curve changed to hyperbolic in the presence of activator (FIG. 6b). The assignment of the SV40 DNA Hpa II site as slow was somewhat arbitrary; the sigmoidal shape of the velocity/saturation curve means that the ability to cleave this site was highly dependent on the concentration of the DNA substrate.

The resistance to cleavage of the Hpa II site in SV40 DNA was not due to methylation. Methylation of this site with Hpa II methylase completely blocked cleavage at that site and no activation by pBR322 DNA was observed (results not shown). Similar results were obtained upon methylation of the Nae I site in M13mp18 DNA.

In contrast to the slow cleavage of Hpa II and Nae I sites, the slow cleavage of a Msc I site in pBR322 is probably due to methylation. That slow site overlaps a dcm methylase site, CC(A or T)GG. Cleavage of pBR322 DNA with Eae I (Py/GGCCPu), which overlaps the Msc I (TGG/CCA) site and is inhibited by 5-meC (methylation inhibition tabulated by M. Nelson and M. McClelland, Nucl. Acids Res 15 suppl., r219 (1987)), demonstrated that three of the four Eae I sites in pBR322 DNA were cleaved; the uncleaved site was the unique Msc I/Eae I recognition site that overlaps the dcm site (not shown). Methylation can explain why this was the only slow or resistant site found that could not be activated by cleavable DNA.

Figure 7A:
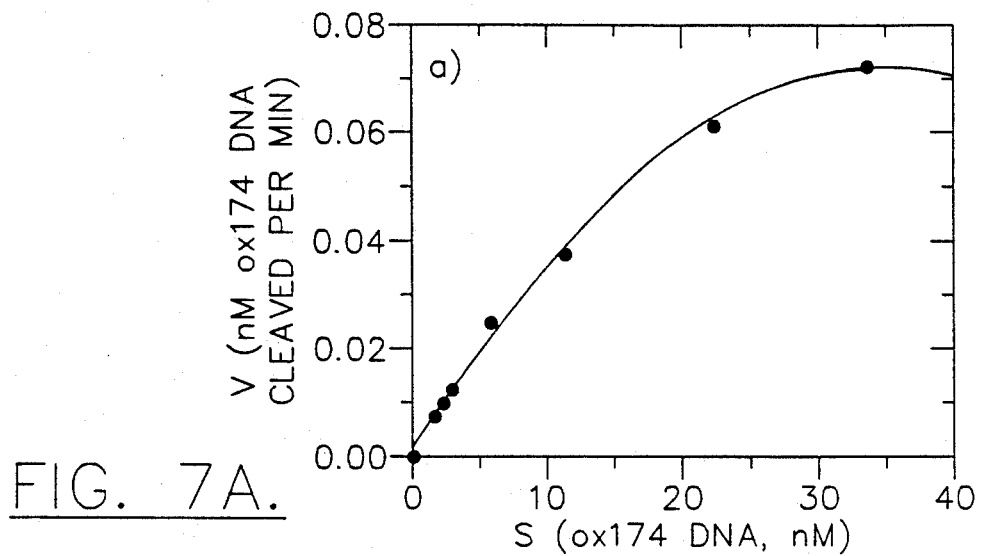
FIG. 7. Kinetics of cleavage for Sac II at two different slow sites. a) V versus S plot for Sac II slow site in φX174 DNA. Variable amounts of substrate were incubated for 40 minutes (37° C.) with 1.0 unit of enzyme in 10 ml reaction volume. b) V versus S plot for Sac II slow site in pMB3 DNA. Variable amounts of substrate were incubated for 40 minutes (37° C.) with 1.6 units of Sac II in 10 ml reaction volume. c) Hill plot for Sac II slow site in pMB3 DNA. The slope of log (v/1-v) versus log S gives the Hill coefficient, a measure of cooperativity.
Figure 7B:
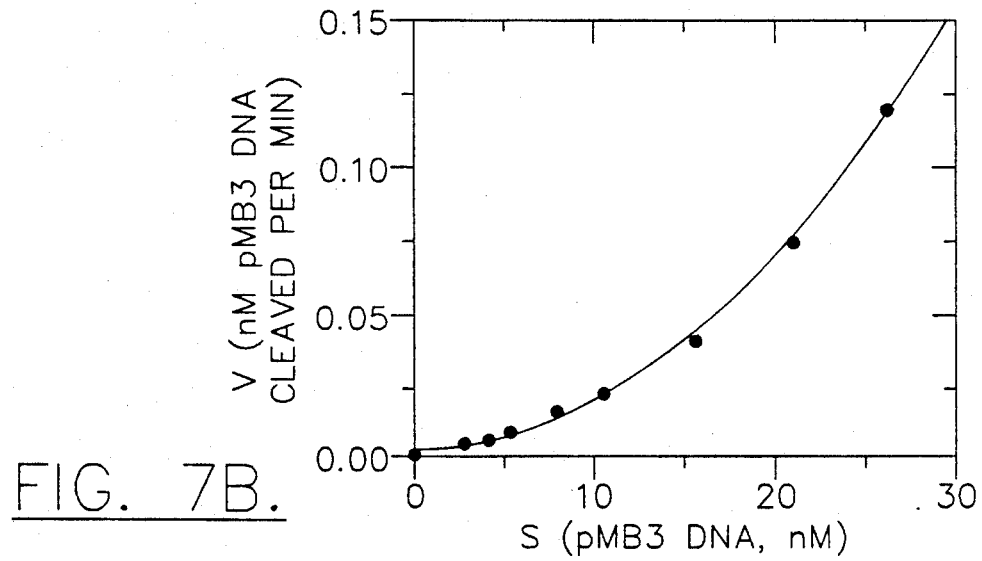
Figure 7C:
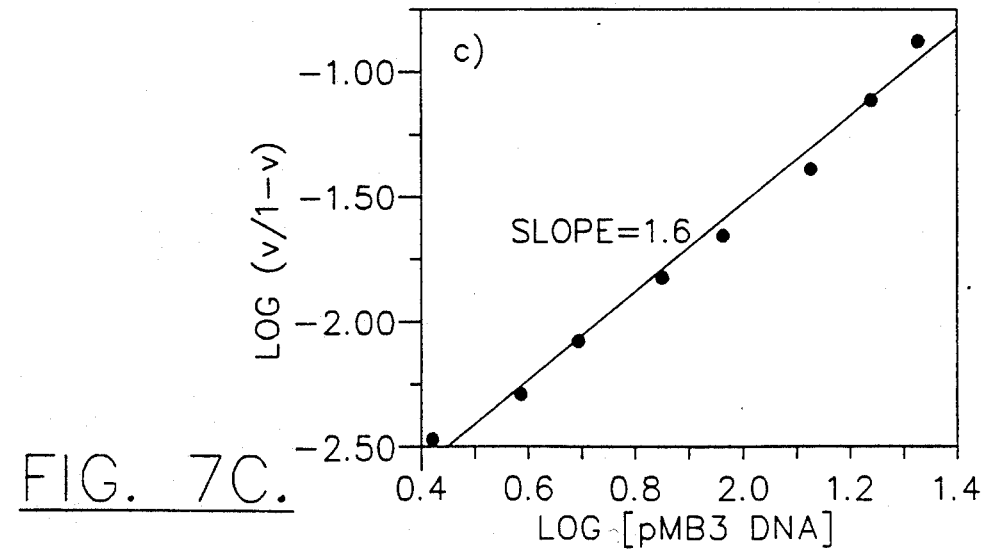

FIG. 7 shows two examples of V (nmols of substrate cleaved/liter/min) versus S (nM) plots for cleavage of two different Sac II slow sites. Cleavage of the Sac II slow site in $\phi$X174 DNA showed the rectangular hyperbola characteristic of Michaelis-Menten kinetics (FIG. 7a). By contrast, Sac II cleavage of the pMB3 DNA slow site showed a sigmoidal dependence on substrate concentration (FIG. 7b). A Hill coefficient of 1.6 was determined (FIG. 7c) for the binding of pMB3 DNA; if we assume that two substrate sites are present on the enzyme, the Hill coefficient indicates 80% cooperativity for substrate binding.

Nae I and Sac II could be activated by cleavable DNA to cleave their slow sites at a faster rate (not shown); the effect was not as strong for Sac II as for Nae I. This is understandable, since the activated and nonactivated saturation curves for Sac II are not that different in terms of rates of cleavage (FIG. 7a vs. FIG. 7b). This small difference could explain the inability to observe activation of Sac II cleavage of pMB3 DNA by lambda DNA. The general inability to activate Sac II cleavage of $\phi$X174 DNA is probably related to the already activated shape of the saturation curve for cleavage of this site; the more active form of the enzyme binds this substrate. In general, we observed that cleavable sites at high molar ratio to the slow sites were required to activate cleavage of slow sites; this is in contrast to the lower molar ratios required to activate cleavage of resistant sites.

Figure 8:
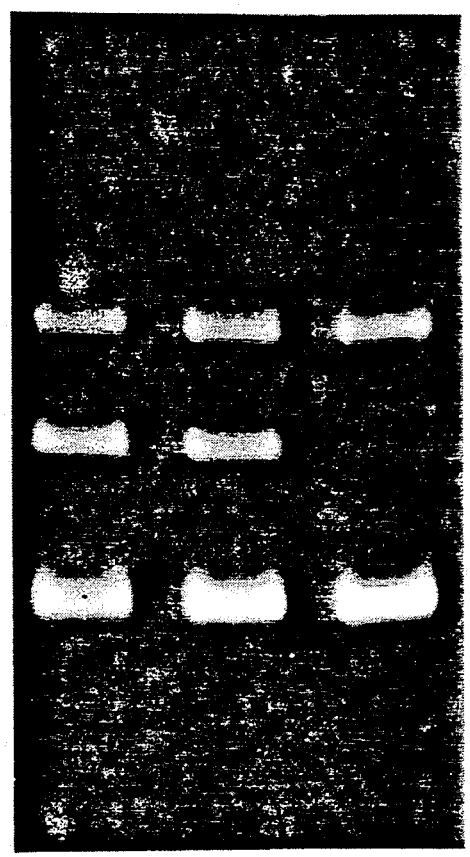
FIG. 8. The effect of spermidine on the cleavage of the Nae I slow site in SV40 DNA. Reaction conditions: Spermidine as indicated, SV40 DNA (2.9 nM) in a 10 ml reaction, 1.1 units of Nae I, $MgCl_2$ (10 mM), NaCl (20 mM), Tris-HCl (pH 8.0) (10 mM), b-mercaptoethanol (5 mM), 100 mg bovine serum albumin per ml. Reactions were incubated for 1 hour at 37° C.

Spermidine Effects. Spermidine was able to activate the cleavage of resistant sites and to increase the rate of cleavage of slow sites. The activation of cleavage of resistant sites by spermidine exhibited activation maxima at concentrations of spermidine between 0.5 and 10 mM (tested at the manufacturer's recommended salt conditions for each enzyme). The effect of spermidine was dependent on the concentration of $Mg^{2+}$ as shown in Example 1 above. FIG. 8 shows Nae I endonuclease digests of the SV40 slow site in the absence and presence of spermidine. Under identical conditions of DNA and enzyme concentration the addition of 2 mM spermidine increased cleavage 40-fold from 0.4% to 17%.

We reported above that the addition of an activating concentration of spermidine to an Nae I cleavage reaction containing activating DNA inhibited cleavage. The experiments were done in the presence of low concentrations of NaCl and $MgCl_w$. We have repeated those experiments at 50 mM NaCl and 10 mM $MgCl_2$. The results remain the same, but the spermidine concentration at which the switch occurs is at 8 mM instead of the 1 mM at low salt concentration (not shown). This agrees with the dependence of the activating effect of spermidine on salt concentration. The effect of spermidine in the presence of activator for Bsp MI, Hpa II, Nar I, or Sac II has not been examined. The effects of spermidine on the kinetics of activation for these enzymes are currently being examined.

C. DISCUSSION

In this Example, 49 restriction enzymes were screened using standard restriction enzyme assays. In addition to Nae I endonuclease, we found that BspM I and Nar I also have recognition sites resistant to cleavage. Furthermore, we found that Hpa II, Nae I, and Sac II endonucleases have slow sites. Cleavage of resistant and slow sites by these enzymes was enhanced by the addition of either cleavable sites in trans or spermidine.

Commercially available DNA substrates with one recognition site per molecule were used to test the activity of restriction enzymes; a substrate with more than one site could obscure the presence of a resistant site because of cis-activation (Example 1 above). The use of readily available DNAs with unique restriction sites enabled us to screen a large number of enzymes. It is possible, however, that some of the 44 enzymes for which only cleavable sites were detected may have other untested substrates with resistant sites. Our observations may, therefore, underestimate the presence of both resistant/slow sites and restriction enzymes whose activity is subject to modulation by DNA.

Resistant and Slow Sites. Kinetic analysis of the cleavage of either resistant or slow substrates by some enzymes indicated two different mechanisms of activation. The enzyme BspM I, as with Nae I, gave hyperbolic substrate saturation curves with varying Vmax and constant Km; the curves were hyperbolic at all activator concentrations studied. In the absence of activator very little cleavage of resistant sites could be detected and cleavage was not significantly increased by increasing substrate concentrations substantially above Km. These results indicate that BspM I, as with Nae I, is an allosteric positive V-system enzyme according to the classic allosteric protein model (J. Monod et al., *J. Mol. Biol.* 12, 88 (1965)), in which the protein contains independent binding sites for activator and substrate and has at least two conformations; substrate has the same affinity for both conformations of the protein, but the two protein conformations differ in their catalytic activity. Activator DNA must have maximum affinity for the more active state of the protein.

The kinetics for the cleavage of substrate by the enzyme Hpa II on the other hand, were sigmoidal with respect to substrate concentration, indicating that substrate binding at the active site was cooperative. With increasing concentrations of DNA activator, the kinetics for cleavage changed from a sigmoidal dependence on substrate concentration to Michaelian hyperbolic; Km decreased with increasing activator concentration, whereas Vmax remained constant. Measurements of Km for Nar I at different activator concentrations showed similar kinetics to Hpa II. These results indicate that Hpa II and Nar I are allosteric positive K-system enzymes, in which these proteins have independent binding sites for substrate and activator and at least two conformations. In contrast to the V-system enzymes, however, both activator and substrate have differential affinities towards the two conformations of protein. The presence of activator increases the affinity of protein for substrate at the active site (Monod et al., supra).

The choice of designating sites for K-system enzymes as either resistant or slow was based on the amount of cleavage at the defined concentration of substrate used to screen all of the enzymes (see Materials & Methods). This choice turned out to be somewhat arbitrary; higher substrate concentrations of originally resistant sites give the appearance of slow sites and very high concentrations may appear to be cleavable by K-system enzymes.

The slow cleavage sites found for Sac II in $\phi$X174 DNA and pMB3 DNA gave differing kinetics; cleavage of pMB3 DNA by Sac II endonuclease was sigmoidal with respect to substrate concentration, whereas cleavage of $\phi$X174 DNA was hyperbolic with respect to substrate concentration. Similar differences in substrate binding were seen for various triphosphonucleosides acting as phosphoryl donors in the deoxythymidine-kinase reaction (R. Okazaki and A. Kornberg, *J. Biol. Chem.* 239, 275 (1964)). With ATP, for example, the rate-concentration curve is strongly cooperative (sigmoidal), whereas with dATP the curves are hyperbolic. Furthermore, CDP converts the ATP sigmoidal curve to hyperbolic indicating allosteric activation (Okazaki & Kornberg, supra). Monod et al. (supra) argue that the deoxythymidine-kinase observations support their model so that "when the binding of two analogous ligands depends very much on steric factors it may be expected that the ratios of the affinities of each ligand towards the two states of the protein will be different. If so, the two ligands might bind to the same sites with widely different interaction coefficients."

Sac II also appears to support this model; homotropic allosteric effects are apparent for Sac II. The Sac II DNA substrates $\phi$X174 DNA and pMB3 DNA apparently have very different relative affinities for the two states of the protein. Activation of cleavage of pMB3 DNA was obtained by the addition of other DNA containing cleavable Sac II sites. This activation indicates activating heterotropic allosteric effects in addition to the homotropic allosteric effects of substrate.

Relative Ability to Activate Cleavage. Determination of the rank order of sites, cleavable, slow, or resistant, required to activate cleavage of any other type of site (Table 4 and Example 1) shows, from our population, that: a) each site susceptible to activation required a more cleavable site to activate its cleavage, and b) the amount of activating site required for activation of cleavage of substrate appeared to be proportional to the cleavability of that substrate. One model that can explain these characteristics assumes that resistant and slow sites, and perhaps cleavable sites as well, differ only in their relative ability to bind to the activator site of their cognate enzymes. According to this model, a higher concentration of cleavable sites is necessary to activate cleavage of a slow site than is necessary to activate cleavage of a resistant site because the cleavable site must compete with the slow site for binding to the activator site of the enzyme.

According to the model, resistant sites do not bind the enzyme activator site so they cannot activate cleavage of any of the sites. Slow sites can potentially activate another slow site or cleavable site, however, the high concentrations required would competitively inhibit substrate cleavage. Cleavable sites theoretically are already fully activated either because they bind to the activation site as well as to the substrate site or because they bind the active conformation of the protein in a manner analogous to the Sac II/$\phi$X174 system discussed above. Thus, it is possible that the class of restriction enzymes that contain an activator site as well as a substrate site is much larger than the five enzymes we have characterized so far.

An exception to the above model is the behavior of Lambda DNA with several of the restriction enzymes. The reason for its inability to be cleaved by Nae I even in the presence of potentially activating DNAs and its inability to activate resistant and slow sites for enzymes that cleave lambda (Table 4) is not known.

Flanking Sequence Effects. Slow and resistant sites must exist because of the effect of sequences outside the recognition sequence. These sequences can interact directly with enzyme. For example, site directed mutagenesis, chemical protection experiments, and X-ray crystallography show that, in addition to bases within the recognition site, bases outside the site are also contacted by Eco RI (A. Lu et al., *J. Biol. Chem.* 256, 13200 (1981); J. McClarin et al., *Science* 234, 1526 (1986). This could be the reason that Eco RI varies up to 10-fold in its ability to cleave the 5 recognition sites in lambda DNA (M. Thomas and R. Davis, *J. Mol. Biol.* 91, 315 (1974)) and the 5 recognition sites in adenovirus DNA (S. Forsblom et al., *Nucleic Acids Res.* 3, 3255 (1976)).

Our results provide evidence for interactions of the restriction enzymes with distant DNA sequences. Comparison of the sequences immediately flanking the several Nae I recognition sequences used as substrates for Nae I endonuclease (Table 4) showed no obvious correlation of sequence with Km differences. In fact, two of the most disparate Kms are for the single Nae I sites whose flanking sequences are almost identical to each other for 126 base pairs downstream and 384 bases upstream from the recognition sequence.

This situation arises for the bacteriophage f1 intergenic region (514 base pairs) engineered into pUC18 to give the vector pUC-f1. The f1 intergenic region contains the Nae I site and is almost identical to its homolog in M13; single base differences occur 86 and 212 base pairs upstream from the Nae I recognition site (D. Hill and G. Peterson, *J. Virol.* 44, 32 (1982)). This region in the context of M13 gives a Km of 2 nM, whereas in the context of pUC-f1 it gives a Km of 42 nM. Thus, in this instance distant sequences affect the relative affinity of the protein for its binding site by 20-fold. We do not know the basis for this interesting effect of distant sequence on Km; we are studying the basis for the resistance to cleavage of the Nae I site in M13 DNA to understand the basis for these apparently long-range effects.

Conclusions. We have shown that the ability of DNA and spermidine to activate Nae I endonuclease from *Nocardia aerocolonigenes* is not unique to this enzyme or to this species. BspM I, Hpa II, Nar I, and Sac II share a similar mechanism. The activating mechanism was found to belong to two different classes; one, for BspM I and Nae I, in which the catalytic activity ($k_{cat}$) of the enzyme is increased by the activator (V-system) and the other, for Hpa II, Nar I, and Sac II, in which the affinity of binding of the resistant substrate is increased by the activator (K-system).

These enzymes have been isolated from four different species of bacteria, Bacillus, Haemophilus, Nocardia, and Streptomyces, suggesting a broader distribution of this regulatory mechanism among bacterial species. In addition, activation has now been extended to slow as well as resistant sites.

EXAMPLE 3

Optimization of Activating sequences

An oligonucleotide duplex having the sequence: GGGTGCCGGCAGGG was synthesized in accordance with standard procedures. See, e.g., Applied Biosystems, User Bulletin: DNA synthesizer Model 380/381 (Issue No. 13-Revised, Apr. 1, 1987). When tested as an activating sequence for Nae I in accordance with the procedures described above, it was found to give 100% activation, making it our best activator sequence. This demonstrates that a variety of flanking sequences are available which are cleavage-permissible.

The scissile linkage of the foregoing sequence is modified in accordance with known procedures to both the methylphosphonate and the phophorothioate to provide cleavage-resistant activating sequences.

EXAMPLE 4

Purification of Restriction Enzymes by Affinity Purification With Immobilized Cleavage Resistant Sites pBR322 DNA is labelled at a unique end by incubating Nde I-linearized pBR322 DNA with bacteriophage T4 DNA polymerase (1.4 units/ug DNA) in 33 mM Tris acetate (pH 7.9), potassium acetate (66 mM), magnesium acetate (10 mM), DTT (0.5 mM), and 100 mg bovine serum albumin per ml at 37° for 30 sec to briefly digest the 3' ends. To this, dNTPs (including biotinylated dCTP) are added to a final concentration of 100 mM each and incubation continued for 2 min. After the reaction is stopped by adding EDTA to 50 mM, the biotinylated DNA is precipitated in ethanol, cut with Pvu II endonuclease to remove one of the labeled ends (this step may be unnecessary), phenol extracted and ethanol precipitated again. At this point the DNA is purified away from unbound biotin nucleotides and directly bound to commercially available avidin-agarose ((Sigma Chem. Co.) or Streptavidin (1 mg/ml) added directly to the reactions for 30 secs at 37° to give DNA with streptavidin tightly coupled to the biotin labeled DNA. The avidin/biotin-labeled DNA is then bound to biotin-agarose (Sigma Chem. Co.) through use of the multiple binding sites on avidin.

The foregoing examples are illustrative of the present invention, and are not to be construed as limiting thereof. The invention is defined by the following claims, with equivalents of the claims to be included therein.

That which is claimed is:

1. A method of cleaving substrate DNA with a restriction enzyme, wherein the substrate DNA is resistant to cleavage by the restriction enzyme, the method comprising:

co-incubating the substrate DNA and the restriction enzyme with an activating DNA sequence; the activating sequence comprising:

an oligonucleotide comprising said restriction enzyme recognition site and cleavage permissible flanking sequences joined directly to both the 5' and 3' ends of said recognition site;

wherein said restriction enzyme is selected from the group consisting of Nae I, Hpa II, Nar I, and Sac II.

2. A method according to claim 1, wherein said oligonucleotide is not more than about 50 nucleotides in length.

3. A method according to claim 1, wherein said oligonucleotide is not more than about 25 nucleotides in length.

4. A method according to claim 1, wherein said oligonucleotide has unphosphorylated ends.

5. A method according to claim 1, wherein said oligonucleotide further comprises a blocking group covalently joined at least one end thereof.

6. A method according to claim 1, wherein said cleavage-permissable flanking sequences are at least three nucleotides long.

7. A method according to claim 1, wherein said cleavage-permissible flanking sequences are at least four nucleotides long.

8. A method of cleaving substrate DNA with a restriction enzyme, wherein the substrate DNA is resistant to cleavage by the restriction enzyme, the method comprising:

co-incubating the substrate DNA and the restriction enzyme with an activating DNA sequence; the activating sequence comprising:

an oligonucleotide comprising said restriction enzyme recognition site wherein said recognition site contains at least one scissile linkage modified to render it incapable of hydrolysis by said restriction enzyme and cleavage permissible flanking sequences joined directly to both the 5' and 3' ends of said recognition site.

9. A method according to claim 8, wherein said at least one scissile linkage which has been modified to render it incapable of hydrolysis by said restriction enzyme has the formula:

wherein X and X' are each independently O or S; and Y is $O^-$, $CH_3$, OR, or $NR_2$ wherein R is lower alkyl; subject to the proviso that X and X' are not simultaneously O when Y is $O^-$.

10. A method according to claim 8, wherein X and X' are O and Y is $CH_3$.

11. A method according to claim 8, wherein Y is $O^-$ and at least one of X and X' is S.

12. A method according to claim 8, wherein both of said scissile linkages have been modified to render them incapable of hydrolysis by said restriction enzyme.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:1:

GCCGGC 6

( 2 ) INFORMATION FOR SEQ ID NO:2:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:2:

CTAGCTGGTG GTGGGCGCCG GCGGTGTGGG CAGCTGGTGA GCT 43

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:3:

TTGGTGGGCG CCGGCGGTGT GGGCA 25

( 2 ) INFORMATION FOR SEQ ID NO:4:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:4:

GGGCGCCGGC GGTG 14

( 2 ) INFORMATION FOR SEQ ID NO:5:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:5:

GCGCCGGCGG                      10

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:6:

CTGGTGGTGG GCGCCGGC            18

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:7:

GCCGGCGGTG TGGGCAGCTG GTG        23

( 2 ) INFORMATION FOR SEQ ID NO:8:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:8:

GGGTGCCGGC CAGGG                15